US005491259A

United States Patent [19]
Grierson et al.

[11] Patent Number: 5,491,259
[45] Date of Patent: Feb. 13, 1996

[54] PROCESS TO PRODUCE AMINOCARBOXYLIC ACIDS CONTAINING LOW RESIDUAL SALT

[75] Inventors: Jeffrey G. Grierson, Lake Jackson; Cameron T. Costain, Angleton; David A. Wilson, Richwood, all of Tex.

[73] Assignee: The Dow Chemical Company, Midland, Mich.

[21] Appl. No.: 305,111

[22] Filed: Sep. 13, 1994

[51] Int. Cl.$^6$ .................................................. C07C 229/00
[52] U.S. Cl. ........................... 562/554; 210/639; 210/653; 210/652; 210/654; 210/655; 562/567; 562/568; 562/571; 562/575
[58] Field of Search .................................. 562/554, 567, 562/568, 571, 575; 210/639, 653, 655, 652, 654

[56] References Cited

U.S. PATENT DOCUMENTS

| | | |
|---|---|---|
| 2,276,986 | 3/1942 | Kemp et al. |
| 2,710,876 | 6/1955 | Krebs et al. |
| 3,450,631 | 6/1969 | Bloch et al. |
| 3,911,080 | 10/1975 | Mehl et al. |
| 3,947,351 | 3/1976 | Asawa et al. |
| 4,067,803 | 1/1978 | Quentin . |
| 4,554,376 | 11/1985 | Fujimoto et al. |
| 4,652,350 | 3/1987 | Cipriano et al. |
| 4,661,257 | 4/1987 | Kreevoy et al. |
| 4,677,065 | 6/1987 | Büchbjerg et al. |
| 4,678,655 | 7/1987 | Twardowski . |
| 4,689,234 | 8/1987 | Ernstrom et al. |
| 4,717,425 | 1/1988 | Lefebvre . |
| 4,728,430 | 3/1988 | DiLeo et al. |
| 4,765,905 | 8/1988 | Kitamura et al. |
| 4,818,409 | 4/1989 | Puetter et al. |
| 4,838,895 | 6/1989 | Galli ............................................. 8/527 |
| 4,861,486 | 8/1989 | Lefebvre . |
| 4,886,889 | 12/1989 | Mattison ................................. 548/497 |
| 4,889,633 | 12/1989 | Pfenninger . |
| 4,933,270 | 6/1990 | Bagchi . |

OTHER PUBLICATIONS

U.S. Patent Application Serial No. 08/236,875 filed on Apr. 29, 1994.
U.S. Patent Application Serial No. 08/167,252 filed on Dec. 14, 1993.
Derwent Abstract 85–207661/34 (J6 0132–604–A), 19 Dec. 1983.
Derwent Abstract 47479 K/20 (J5 8058–112), 3 Oct. 1981.
Derwent Abstract 11215T–AB (BE 771042–Q), 12 Aug. 1970.
Derwent Abstract 26509B/14 (FR 2396–020), 1 Jul. 1977.
Derwent Abstract 87–350884/50 (J6 2252–465–A), 24 Apr. 1986.
Derwent Abstract 06835B/04 (J5 3142–598), 13 May 1977.
Derwent Abstract 83–758901/36 (WO 8302–905–), 26 Feb. 1982.

*Primary Examiner*—Michael L. Shippen

[57] ABSTRACT

A method for producing an aqueous solution of an aminocarboxylic acid from an aqueous solution of an alkali metal salt of the aminocarboxylic acid is disclosed. The first step of the method is to adjust the pH of the aqueous solution of the alkali metal salt of the aminocarboxylic acid to between about 1.0 and about 3.0. This is done by adding a monovalent inorganic acid to the aqueous solution of the alkali metal salt of the aminocarboxylic acid to form an aqueous feed solution containing protonated aminocarboxylic acid and an inorganic alkali salt having an inorganic anion and an alkali metal cation. The second step of the method is to pass the aqueous feed solution through at least one membrane using a diafiltration process to separate the aqueous feed solution into an aqueous permeate solution, containing the alkali metal cation, and an aqueous retentate solution containing the aminocarboxylic acid.

17 Claims, No Drawings

PROCESS TO PRODUCE AMINOCARBOXYLIC ACIDS CONTAINING LOW RESIDUAL SALT

This invention pertains to a method to produce aminocarboxylic acids containing low residual salt, and more particularly to methods of producing aminocarboxylic acids from an aqueous solution of an alkali metal salt of the aminocarboxylic acid.

BACKGROUND OF THE INVENTION

Aminocarboxylic acid salts can be synthesized by a number of known methods. Previously, the salts of certain aminocarboxylic acids had been converted to aminocarboxylic acids by using conventional acid crystallization methods or by electrochemical processes. These methods were expensive and/or not well suited because of the relatively high water solubility of the acid in the presence of sodium ions. Thus, using conventional methods, the production of aminocarboxylic acids cost about three times what their corresponding salts cost.

Yet, there is a strong need for these aminocarboxylic acids, including for example health and industrial uses. Further, N-(hydroxyethyl)ethylenediaminetriacetic acid (HEDTA acid) has general broad applications as an industrial cleaner, for boiler cleaning and treatment, and as a micronutrient. Further, technology is needed to recover HEDTA acid from spent boiler cleaning applications.

An alkali metal salt of aminocarboxylic acid is an aminocarboxylic acid which has had one or more of its ionizable hydrogen atoms (on a COOH group) replaced by an alkali metal such as sodium or potassium to form a salt. Thus, aminocarboxylic acids salts are converted into their respective aminocarboxylic acids, including N-(hydroxyethyl)-ethylenediaminetriacetic acid (hereinafter referred to as HEDTA acid), diethylenetriaminepentaacetic acid, hydroxyethyliminodiacetic acid, nitrilotriacetic acid, and glycine. These structures are very large when compared to monovalent alkali metal ions such as sodium and monovalent anions such as chlorine. This size differential makes diafiltration possible. Diafiltration is a constant volume washing process in which a membrane is used to selectively remove smaller molecules and ions, and/or exchange solvent while retaining the larger molecules and ions in the feed solution.

The following patents are representative of the pertinent art. U.S. Pat. No. 4,889,663 issued Dec. 26, 1989 to Pfenninger. It discloses the use of diafiltration to separate waste water into a disposable organic free aqueous permeate effluent portion and an aqueous retentate portion that is concentrated with organic compounds.

U.S. Pat. No. 4,818,409 issued Apr. 4, 1989 to Puetter et al. discloses a method for obtaining aqueous solutions of organic acids or bases which uses an ion exchange membrane to obtain aqueous solutions from salts of the same.

U.S. Pat. No. 4,765,905 issued Aug. 23, 1988 to Kitamura et al. discloses a method for recovering acids from an aqueous solution of a mixture of the acids and metal salts by dialysis using a fluorinated anion exchange membrane made of a copolymer having repeating units of a given formula.

Japanese Patent No. J5 8058-112 issued Apr. 6, 1983 to Tokuyama Soda discloses the use of a multistage dialysis to reclaim or purify various inorganic and organic acids from their metallic salts. Another Japanese patent, J6 0132-604-A, issued Jul. 15, 1985 to Toray Engineering discloses a method for concentrating and recovering valuable organic compounds also containing inorganic salt by desalting using membrane-separation treatment under an operating pressure above the osmotic pressure of the aqueous solution. Dilution water is added during the treatment to keep the settled level of the starting tank. This patent thus discloses a salt removal process.

Such processes represent older, more costly, less efficient ways of converting aminocarboxylic acids salts to aminocarboxylic acids. The present invention is directed to an improved method of converting aminocarboxylic acid salts.

It would be desirable to provide an improved method of converting aminocarboxylic acid salts to aminocarboxylic acids. It would be advantageous to have a cheap, efficient, environmentally safe, easily applied, and improved method of converting aminocarboxylic acid salts into their corresponding aminocarboxylic acids. The present invention is directed to this need.

It would also be desirable to provide an improved method of converting VERSENOL ™ 120 (the trisodium salt of N-(hydroxyethyl)-ethylenediaminetriacetic acid) to HEDTA acid.

SUMMARY OF THE INVENTION

In accordance with the preferred embodiment of the invention, these and other desired features and advantages are addressed as follows. A method for producing an aqueous solution of an aminocarboxylic acid from an aqueous solution of an alkali metal salt of the aminocarboxylic acid is disclosed. The first step of the method is to adjust the pH of the aqueous solution of the alkali metal salt of the aminocarboxylic acid to between about 1.0 and about 3.0. This is done by adding a monovalent inorganic acid to the aqueous solution of the alkali metal salt of the aminocarboxylic acid to form an aqueous feed solution containing protonated aminocarboxylic acid and an inorganic alkali salt having an inorganic anion and an alkali metal cation. The second step of the method is to pass the aqueous feed solution through at least one membrane using a diafiltration process to separate the aqueous feed solution into an aqueous permeate solution containing the alkali metal cation and an aqueous retentate solution containing the aminocarboxylic acid.

DETAILED DESCRIPTION OF THE INVENTION

The present invention discloses an improved method for producing an aqueous solution of an aminocarboxylic acid from an aqueous solution of an alkali metal salt of the aminocarboxylic acid. The first step of the method is to adjust the pH of the aqueous solution of the alkali metal salt of the aminocarboxylic acid to a pH less than or equal to the isoelectric point of the aminocarboxylic acid. Generally for an aminocarboxylic acid compound, this pH is preferably between about 1.0 and about 3.0, and more preferably for HEDTA between about 1.9 and 2.3. If higher pH levels are used, the aminocarboxylic acid salt will not generally be maintained in a completely protonated acid form so that all of the sodium ions are dissociated and available for removal. Lower pH solutions can be diafiltrated but with disadvantageously more difficulty and expense to use and to maintain. Additionally, safety and environmental concerns motivate against using lower pH levels with the associated excess acid.

The alkali metal salt used is suitably one that has replaced all available hydrogen dissociation sites with alkali metal atoms, or is optionally one that has only some such available sites replaced with alkali metal atoms. The level of replacement will not effect the process.

The pH of the aqueous solution of the alkali metal salt of the aminocarboxylic acid is adjusted by adding a monovalent inorganic acid to the aqueous solution. Preferably, the monovalent inorganic acid is selected from the group consisting of the hydrogen halides, and nitric acid. Most preferably, for any aminocarboxylic acid compound, the monovalent inorganic acid is hydrogen chloride. Divalent acids such as sulfuric acid do not work well for the purposes of this invention, because the negative ions involved are too large and too highly charged to easily pass through the diafiltration membrane. The adjustment of the pH of the aqueous solution of the alkali metal salt of the aminocarboxylic acid results in an aqueous feed solution containing protonated aminocarboxylic acid along with an inorganic alkali salt having an inorganic anion and an alkali metal cation.

It is also preferred that the aqueous feed solution have an aminocarboxylic acid alkali metal salt concentration sufficient to supply a high concentration driving force for the displaced alkali metal salts so that they are driven through the diafiltration membrane, yet insufficient to exceed the aminocarboxylic solubility limit at the membrane/solution interface. As shown in TABLES 1-4, process efficiency is determined by the difference between the concentration of alkali metal salts in the permeate and the concentration of the aminocarboxylic acid in the permeate at any time. This difference is larger during the initial stages of the process, when the concentrations of alkali metal salts in the feed solution are larger. Since little aminocarboxylic acid is lost, its concentration is essentially constant. Preferably the feed concentration of aminocarboxylic acid is between about 1 and about 25 weight percent for aminocarboxylic acids in general, more preferably from about 6 to about 15 weight percent especially for HEDTA. Although feed concentration is not significant for laboratory experiments, it is more important in full scale production systems. Optimal feed concentrations balance osmotic forces against increased membrane surface area, make-up water use and other factors. Such balance is within the skill in the art. The examples hereafter reveal the above range to be desirable.

Aqueous feed solution temperature is also an important variable. Advantageously, aqueous feed solution temperature is maintained sufficiently high to maintain the aminocarboxylic acids in solution, preferably between about 10° C. to 50° C., more preferably between about 35 and 50° C., most preferably between about 40 and 45° C. Typically, aminocarboxylic acid salts have good solubility in water and typically increase in solubility with increasing temperature. Conversely, aminocarboxylic acids themselves typically have lesser solubility in water. The preferred temperatures help keep the acids in solution and, thus, help avoid membrane fouling problems.

For example, HEDTA acid has a 6 percent solubility at 20° C., although it exhibits 70 percent solubility at 90° C. Keeping the aqueous feed solution warm helps to keep the HEDTA acid in solution. As some of the examples below indicate, the normal solubility curves of the aminocarboxylic acids used (HEDTA acid in the examples) helps in collecting a very pure product by concentrating the end feed at a high temperature and then cooling it and collecting the crystallized final product. The preferred temperature ranges are based upon a variety of these factors.

The present invention is applicable to any aminocarboxylic acid. Preferably, however, the aminocarboxylic acid is selected from the group consisting of N-(hydroxyethyl)-ethylenediaminetriacetic acid, diethylenetriaminepentaacetic acid, and hydroxyethyliminodiacetic acid, dihydroxyethyl glycine, iminodiacetic acid, glycine and mixtures thereof.

After pH adjustment, the next step of the method of the present invention is passing the aqueous feed solution through at least one membrane using a diafiltration process to separate the aqueous feed solution into an aqueous permeate solution containing the alkali metal cation and an aqueous retentate solution containing the aminocarboxylic acid. Any appropriate diafiltration process is suitably used, as described in further detail hereinafter.

In diafiltration, any diafiltration membrane or membrane system is suitably used, for instance, membranes made of polyamide, polysulfone, nylon, cellulose acetate, acrylnitrile, polypropylene or polyvinylidene fluoride (PVDF). Preferably, however, the membrane is selected to achieve a rejection rate of the inorganic salt anion of at most about 40 percent and a rejection rate of the aminocarboxylic acid of at least about 94 percent. Most preferably, the membrane is chosen to achieve a rejection rate of the inorganic anion of at most about 20 percent and a rejection rate of the aminocarboxylic acid of at least about 98 percent.

The preferred membranes are those formed of polyamide. Thus, as the following examples show, the inventors have had particular success with polyamide nanofiltration thin film composite membranes commercially available from Filmtec™ Corporation of Minnesota, a subsidiary of The Dow Chemical Company, under the trade designation Filmtec™ NF-40 and NF-20. Lower product losses are observed when using the Filmtec™ NF-40 polyamide membrane. These membranes are selected for their high rejection rate of monovalent ions. The membrane used is advantageously acid resistant, at least to the acidity of the aminocarboxylic acid and monovalent inorganic acid used.

In a preferred embodiment, it is desirable to recycle at least a portion of the aqueous retentate solution to the aqueous feed solution to be refiltered to achieve a higher overall rejection rate of the aminocarboxylic acid. Any appropriate recycling system may be used.

It is more preferred to cool a portion of the aqueous retentate solution, advantageously to less than about 30° C to cause crystals of aminocarboxylic acid to precipitate out of the cooled portion of the aqueous retentate solution. These precipitated crystals are optionally filtered out of the cooled portion of the aqueous retentate solution, and the remaining aqueous retentate solution is returned to the aqueous feed solution.

In the following examples, a feed tank is used which contains an aqueous solution of an aminocarboxylic acid alkali metal salt. A second feed tank holds make-up water. The aqueous solution of the aminocarboxylic acid alkali metal salt is drawn off and mixed with the make-up water to adjust the pH of the aqueous solution of the aminocarboxylic acid alkali metal salt to a predetermined operating pH. The adjusted mixture is then pumped, under pressure, through the designated membrane, resulting in an aqueous permeate solution containing the alkali metal cation and an aqueous retentate solution containing the aminocarboxylic acid. The aqueous retentate solution is recycled until the indicated level of desalting has occurred. After that, the aqueous retentate solution is cooled to precipitate crystalline aminocarboxylic acid product out of the solution. The crystals are then removed, and remaining aqueous retentate solution is returned to the feed tank for further processing. A heater is used in most examples.

The following examples and summaries of experiments illustrate the present invention, but are not limiting to it. All examples (Ex.) are designated numerically and all comparative samples (C.S.) which are not examples of the invention, are designated alphabetically. All ratios, percentages, and parts are by weight unless otherwise indicated.

EXAMPLES 1–4

A recirculating heater is started and brought to an operating temperature of 45° C. The feed tank is filled with a test solution consisting of 300g of the trisodium salt of N-hydroxyethyl-ethylenediaminetriacetic acid (500 g for Example 3), 850 g deionized water and enough (37.5 weight percent HCl solution) HCl to bring the pH down to 2.0. The aminocarboxylic acid salt is dissolved in the deionized water before the HCl addition. Then enough deionized water is added to bring the total weight to 1200 grams. A variable speed feed pump is started and feed is recirculated at minimum back pressure that is for five minutes. An initial feed sample of 200 g is removed from the feed tank for analysis. The operating pressure as listed in each table is then set, and permeate is recycled back to the feed tank. After 5–10 minutes of permeate recycling to establish steady state conditions, the run is initiated by routing the permeate stream to a graduated cylinder. Initial time, temperature, pressure and flow rate are recorded. Permeate volume is recorded and composited for samples every 200 ml along with the time to collect the permeate, pressure and temperature. The feed is maintained at a constant volume by replacing every 100 milliliters of collected permeate with the same volume of deionized water. The pH is periodically checked to determine whether or not to add deionized water or acid balanced deionized water (pH=2.0 using HCl) as a means of controlling the feed pH at 2.0. The procedure is repeated until the desired level of washing is reached. While the process can be stopped after as little as about 1% removal of Na$^+$ or continued until the Na$^+$ is almost totally removed (about 99.9 mole percent), these examples are continued to the degree of removal indicated by the ratio of final concentration of Na$^+$ to original concentration of Na$^+$ given in the tables. The pump is then shut off and then feed is drained out of the system. Care is taken to drain all low spots in both feed and permeate lines.

Four exploratory batch examples are performed at two different feed concentrations using either pH adjusted or straight deionized make-up water. The membrane used in the work is a membrane which consists of a thin coating of a polyamide polymer as the active layer on top of a porous backing material, commercially available from Film Tec Corp. under the trade designation Filmtec™ NF-40. To test the material for gross leaks and proper installation in a membrane holder, a sodium chloride rejection test is performed. Rejection of the salt from a dilute (<1 weight percent) solution is 39.3 percent at an applied pressure of 300 PSIG (pounds per square inch gauge) (2068 pKa). This is close to the nominal factory specification for this material, indicating the membrane and installation are satisfactory.

TABLE 1 is a table showing permeate concentration versus total permeate volume corresponding to Example 1.

TABLE 2 is a table showing permeate concentration versus total permeate volume corresponding to Example 2.

TABLE 3 is a table showing permeate concentration versus total permeate volume corresponding to Example 3.

TABLE 4 is a table showing permeate concentration versus total permeate volume corresponding to Example 4.

TABLE 1

Experimental Data for VERSENOL ™ 120 HEDTA Diafiltration Example 1
Operating Presure: 500 psig (3447 kPa)
Temperature: 45° C.

| Sample | | Weight Feed (g) | Total Carbon (ppm) | Chloride (ppm) | Sodium (ppm) |
|---|---|---|---|---|---|
| | Initial Feed | 1000 | 40797 | 37940 | 25780 |
| | End Feed | 940 | 40063 | 11736 | 10320 |

| Permeate Example # | Permeate Removed (ml) | Permeate Concentrations | | | Make-up Water Added (ml) |
|---|---|---|---|---|---|
| | | TC (ppm) | Chloride (ppm) | Sodium (ppm) | |
| 1.1 | 200 | 2194 | 33977 | 23230 | 200 |
| 1.2 | 200 | 1908 | 27346 | 18820 | 200 |
| 1.3 | 400 | 1722 | 19983 | 13720 | 400 |
| 1.4 | 400 | 1550 | 13198 | 9180 | 400 |
| 1.5 | 200 | 1588 | 9858 | 6740 | 200 | ppm is parts by million by weight
TC is total organic carbon in permeate

TABLE 2

Experimental Data for VERSENOL ™ 120 HEDTA Diafiltration Example 2
Operating Presure: 500 psig (3447 kPa)
Temperature: 45° C.

| Sample | | Weight Feed (g) | Total Carbon (ppm) | Chloride (ppm) | Sodium (ppm) | |
|---|---|---|---|---|---|---|
| | Initial Feed | 999 | 36718 | 36348 | 27264 | |
| | End Feed | 948 | 36083 | 12784 | 7944 | |

| Permeate Example # | Permeate Removed (ml) | Permeate Concentrations | | | Make-up Water Added (ml) | Make-up Water Chloride Concentration (ppm) |
|---|---|---|---|---|---|---|
| | | TC (ppm) | Chloride (ppm) | Sodium (ppm) | | |
| 2.1 | 200 | 1455 | 31729 | 20930 | 200 | 0 |
| 2.2 | 200 | 1198 | 25945 | 16047 | 200 | 0 |
| 2.3 | 200 | 1020 | 20747 | 13391 | 200 | 0 |

TABLE 2-continued

Experimental Data for VERSENOL ™ 120 HEDTA Diafiltration Example 2
Operating Presure: 500 psig (3447 kPa)
Temperature: 45° C.

| 2.4 | 200 | 875 | 16864 | 10405 | 200 | 0 |
| 2.5 | 200 | 753 | 13665 | 8480 | 200 | 0 |
| 2.6 | 200 | 637 | 11270 | 6744 | 200 | 0 |
| 2.7 | 200 | 548 | 9148 | 5222 | 200 | 0 | ppm is parts per million by weight
TC is total organic carbon

TABLE 3

Experimental Data for VERSENOL ™ 120 HEDTA Disfiltration Examples #3
Operating Pressure: 650 psig (4481 kPa)
Temperature: 45° C.

| Sample | | Weight Feed (g) | Total Carbon (ppm) | Chloride (ppm) | Sodium (ppm) |
| --- | --- | --- | --- | --- | --- |
| | Initial Feed | 999 | 65290 | 57136 | 36545 |
| | End Feed | 942 | 64396 | 15185 | 8693 |

| Permeate Example # | Permeate Removed (ml) | Permeate Concentrations | | | Make-up Water Added (ml) | Make-up Water Chloride Concentration (ppm) |
| --- | --- | --- | --- | --- | --- | --- |
| | | TC (ppm) | Chloride (ppm) | Sodium (ppm) | | |
| 3.1 | 200 | 2732 | 61011 | 38690 | 200 | 1000 |
| 3.2 | 200 | 2229 | 48855 | 32960 | 200 | 1000 |
| 3.3 | 200 | 1850 | 37847 | 22917 | 200 | 1000 |
| 3.4 | 200 | 1522 | 29068 | 17983 | 200 | 1000 |
| 3.5 | 200 | 1316 | 23083 | 14457 | 200 | 1000 |
| 3.6 | 200 | 1160 | 18550 | 11402 | 200 | 1000 |
| 3.7 | 200 | 1052 | 14740 | 9148 | 200 | 1000 | ppm is parts per million by weight
TC is total organic carbon

TABLE 4

Experimental Data for VERSENOL ™ 120 HEDTA Diafiltration - Example 4
Operating Pressure: 600 psig (4136 kPa)
Temperature: 45° C.

| Sample | | Weight Feed (g) | Total Carbon (ppm) | Chloride (ppm) | Sodium (ppm) |
| --- | --- | --- | --- | --- | --- |
| | Initial Feed | 994 | 35226 | 36940 | 24210 |
| | Final Feed | 940 | 34681 | 5571 | 2873 |

| Permeate Example # | Permeate Removed (ml) | Permeate Concentrations | | | Make-up Water Added (ml) | Make-up Water Chloride Concentration (ppm) |
| --- | --- | --- | --- | --- | --- | --- |
| | | TC (ppm) | Chloride (ppm) | Sodium (ppm) | | |
| 4.1 | 200 | 1403 | 30314 | 19954 | 200 | 1086 |
| 4.2 | 200 | 1167 | 25033 | 16161 | 200 | 1086 |
| 4.3 | 200 | 978 | 20038 | 12916 | 200 | 1086 |
| 4.4 | 200 | 828 | 16282 | 10659 | 200 | 1086 |
| 4.5 | 200 | 710 | 13423 | 8574 | 200 | 1086 |
| 4.6 | 200 | 614 | 11255 | 7051 | 200 | 0 |
| 4.7 | 200 | 546 | 9477 | 6051 | 200 | 0 |
| 4.8 | 200 | 479 | 7918 | 4281 | 200 | 0 |
| 4.9 | 200 | 432 | 6750 | 4104 | 200 | 0 |

TABLE 4-continued

Experimental Data for VERSENOL ™ 120 HEDTA Diafiltration - Example 4
Operating Pressure: 600 psig (4136 kPa)
Temperature: 45° C.

| | | | | | | |
|---|---|---|---|---|---|---|
| 4.10 | 200 | 414 | 5838 | 3540 | 200 | 0 |
| 4.11 | 200 | 371 | 5092 | 3124 | 200 | 1086 |
| 4.12 | 200 | 360 | 4504 | 2731 | 200 | 1086 |
| 4.13 | 200 | 339 | 4124 | 2348 | 200 | 1086 |
| 4.14 | 200 | 314 | 3741 | 2090 | 200 | 1086 |
| 4.15 | 200 | 308 | 3396 | 1854 | 200 | 1086 |
| 4.16 | 200 | 291 | 3138 | 1580 | 200 | 1086 |
| 4.17 | 200 | 284 | 2928 | 1421 | 200 | 0 |
| 4.18 | 200 | 276 | 2655 | 1260 | 200 | 0 |
| 4.19 | 200 | 267 | 2407 | 1157 | 200 | 1086 |
| 4.20 | 200 | 264 | 2231 | 1013 | 200 | 1086 | ppm is parts per million by weight
TC is total organic carbon

The experimental data is presented in Tables 1–4. Note that in Examples 1 and 2, the water Cl⁻ concentration is 0, indicating that the make up water is not acid balanced with HCl, whereas in Examples 3 and 4 it is acid balanced. The sodium removals at constant total permeate volume are highest for Example 3. This is to be expected because it has the highest driving force due to an initial feed concentration that is almost twice that of the other runs. It is also Example 3 that has shown the potential for fouling due to crystallization which is not surprising in view of the relatively high end feed HEDTA acid concentration. Overall sodium removal is highest for Example 4, because the amount of diafiltration is highest for this experiment.

The end feed from Example 3 has crystal formation after cooling to room temperature and equilibrating overnight. A 24.2 g sample crystals are collected from 995 g of end feed. The crystals analyze as 180 ppm Na$^+$ and 380 ppm Cl$^-$ by weight of dry crystal or a 99.7 percent Na$^+$ reduction with respect to the initial feed. This corresponds to 18 ppm Na$^+$ and 380 ppm Cl$^-$ in a 10 percent HEDTA acid solution.

By way of comparison, the end feed solution for Example 3 would result in 200 times the Na$^+$ and Cl$^-$ concentrations, according to Table 3, if it were diluted to a 10 percent HEDTA acid solution. Furthermore, in the crystal, the Na$^+$ to Cl$^-$ ratio indicates that all of the sodium is tied up as NaCl with the remaining residual Cl$^-$ as HCl. Therefore, there is a high probability that as diafiltration is continued there should be proportionately lower concentrations of Na$^+$ and Cl$^-$ found in the crystals.

In an attempt to crystallize material from the initial feed before diafiltration, no crystal is formed even near 0° C. This suggests that crystallization can be used in conjunction with diafiltration as a means of obtaining low Na HEDTA acid. While HEDTA acid is used in these examples, the observations and conclusions are true for other aminocarboxylic acids, particularly those listed as preferred for the practice of this invention.

What is claimed is:

1. A method for producing an aqueous solution of an aminocarboxylic acid from an aqueous solution of an alkali metal salt of the aminocarboxylic acid, the method comprising:

adjusting the pH of the aqueous solution of the alkali metal salt of the aminocarboxylic acid to between about 1.0 and about 3.0 by adding a monovalent inorganic acid to the aqueous solution of the alkali metal salt of the aminocarboxylic acid to form an aqueous feed solution containing protonated aminocarboxylic acid and an inorganic alkali salt having an inorganic anion and an alkali metal cation; and passing the aqueous feed solution through at least one membrane using a diafiltration process to separate the aqueous feed solution into an aqueous permeate solution containing the alkali metal cation and an aqueous retentate solution containing the aminocarboxylic acid.

2. The method of claim 1, wherein the aqueous feed solution has an adjusted pH of between about 1.9 and 2.3.

3. The method of claim 1, wherein the aqueous feed solution has an aminocarboxylic acid alkali metal salt concentration of between about 1 to 25 weight percent.

4. The method of claim 1, wherein the aqueous feed solution has an aminocarboxylic acid alkali metal salt concentration from about 6 to about 20 weight percent.

5. The method of claim 1, wherein the aqueous feed solution has an aminocarboxylic acid alkali metal salt concentration of between about 9 to 15 weight percent.

6. The method of claim 1, wherein the aqueous feed solution is maintained at a temperature of from about 10° to about 50° C.

7. The method of claim 1, wherein the aqueous feed solution is maintained at a temperature of from about 35° to about 50° C.

8. The method of claim 1, wherein the aqueous feed solution is maintained at a temperature of between about 40° to 45° C.

9. The method of claim 1, wherein the aminocarboxylic acid is selected from the group consisting of N-(hydroxyethyl)-ethylenediaminetriacetic acid, diethylenetriaminepentaacetic acid, hydroxyethyliminodiacetic acid, dihydroxyethyl glycine, iminodiacetic acid, glycine and mixtures thereof.

10. The method of claim 1, wherein the membrane chosen is able to achieve a rejection rate of the inorganic anion of at most about 40 percent and a rejection rate of the aminocarboxylic acid of at least 94 percent.

11. The method of claim 1, wherein the membrane chosen is able to achieve a rejection rate of the inorganic anion of at most about 20 percent and a rejection rate of the aminocarboxylic acid of at least about 98 percent.

12. The method of claim 1, wherein the membrane is formed of polyamide, polysulfone, nylon, cellulose acetate, acrylnitrile, polypropylene or polyvinylidene fluoride (PVDF).

13. The method of claim 12, wherein the membrane is formed of polyamide.

14. The method of claim 1, wherein the monovalent inorganic acid is selected from the group consisting of the hydrogen halides, and nitric acid.

15. The method of claim 1, wherein the monovalent inorganic acid is hydrogen chloride.

16. The method of claim 1, further comprising recycling at least a portion of the aqueous retentate solution to the aqueous feed solution to be refiltered to achieve a higher yield of the aminocarboxylic acid.

17. The method of claim 1, further comprising cooling a portion of the aqueous retentate solution to less than a solubility limit of the aminocarboxylic acid to cause crystals of aminocarboxylic acid to precipitate out of the cooled portion of the aqueous retentate solution, filtering the crystals formed thereby from the cooled portion of the aqueous retentate solution, and recycling the filtered aqueous retentate solution into the aqueous feed solution.

* * * * *